United States Patent [19]
Long et al.

[11] Patent Number: 5,164,945
[45] Date of Patent: Nov. 17, 1992

[54] LASER DEVICE WITH INTERMEDIATE REFRACTION INDEX LAYER FOR REDUCED FRESNEL LOSSES

[75] Inventors: Gary Long, Cincinnati; Arnold H. Deutchman, Columbus, both of Ohio

[73] Assignee: Laser Centers of America, Inc., Cincinnati, Ohio

[21] Appl. No.: 724,019

[22] Filed: Jul. 1, 1991

[51] Int. Cl.$^5$ .............................................. H01S 3/30
[52] U.S. Cl. ........................................ 372/6; 385/15; 385/31; 385/39; 385/49
[58] Field of Search ................ 372/6; 385/15, 31, 39, 385/49; 128/303.1

[56] References Cited

U.S. PATENT DOCUMENTS

| | | | |
|---|---|---|---|
| 4,126,136 | 11/1978 | Auth et al. | 128/303.1 |
| 4,627,435 | 12/1986 | Hoskin | 128/303.1 |
| 4,693,244 | 9/1987 | Daikuzono | 128/303.1 |
| 4,736,743 | 4/1988 | Daikuzono | 128/4 |
| 4,773,413 | 9/1988 | Hussein et al. | 128/303.1 |
| 4,832,979 | 5/1989 | Hoshino | 427/38 |
| 4,878,725 | 11/1989 | Hessel et al. | 385/15 |
| 4,890,290 | 12/1989 | Hawkins, II | 372/6 |
| 4,941,726 | 7/1990 | Russell et al. | 372/6 |
| 4,992,298 | 2/1991 | Deutchman et al. | 427/38 |
| 4,994,060 | 2/1991 | Rink et al. | 606/28 |
| 5,018,817 | 5/1991 | Suzuki et al. | 385/49 |

FOREIGN PATENT DOCUMENTS 0138411 4/1985 European Pat. Off. .

OTHER PUBLICATIONS

Informational material entitled "Ion Implantation (Advanced Technologies for Surface Entineering)", from BeamAlloy Corporation of Dublin, Ohio, 1989.
Informational literature entitled "Surface Engineering-R and D Services", from BeamAlloy Corporation of Dublin, Ohio.
Article entitled "Ion Nitriding and Nitrogen Ion Implantation: Process Characteristics and Comparisons", by Deutchman et al., Industrial Heating, Jan. 1990, pp. 32-35.
Article entitled "Practical Applications of Ion Beam Mixing: A New Surface Treatment Technique", by Deutchman et al., Industrial Heating, Feb. 1988, pp. 30 and 31.
Article entitled "Deposition-A Gem of a Process", by Deutchman et al., Advanced Materials and Processes Jun. 1989, pp. 29-33.
Article entitled "Application and Utilit of Industrial Diamond-Like Films", by Deutchman et al., Industrial Heating, Jul. 1988, pp. 12-14.

*Primary Examiner*—Georgia Y. Epps

[57] ABSTRACT

A thin layer of a material having a refractive index that varies non-abruptly between the refractive indices of an optic fiber and a tip element in a laser device significantly reduces Fresnel losses where the optic fiber meets the tip element. The layer is readily created by either an ion beam mixing process or by an ion beam enhanced deposition (IBED) process for forming a layer of varying refractive index and comprising a ceramic material such as silica, very securely bonded into the laser light energy receiving end of the tip element which may conveniently be made of a ceramic material such as YAG, silica or sapphire. Greater utility of such a tip element is realized by providing an ohmic heating layer over a part of the tip element. In another aspect of this invention, the tip element is provided with an additional layer comprising a high temperature melting point material at an energy delivery end, applied either by the ion mixing process or the IBED process, to absorb and convert laser light into thermal energy for localized heating, e.g., to vaporize, cauterize, or coagulate tissues in a surgical procedure.

36 Claims, 4 Drawing Sheets

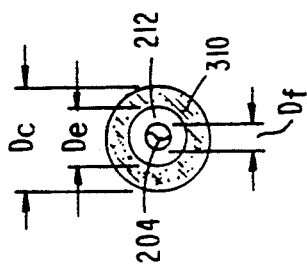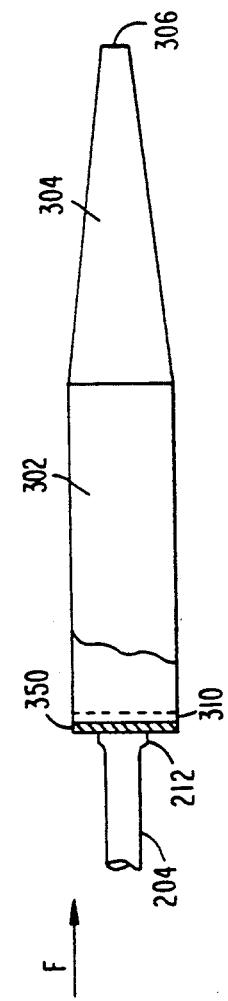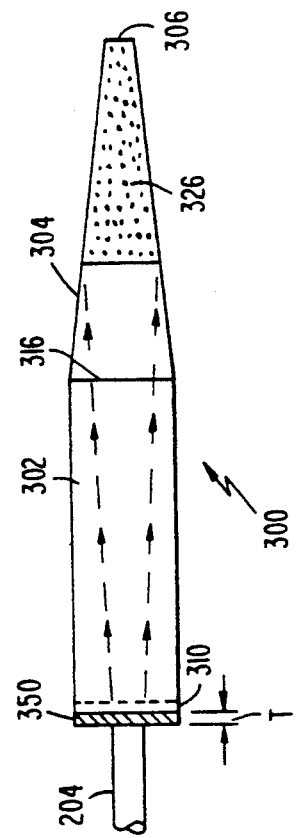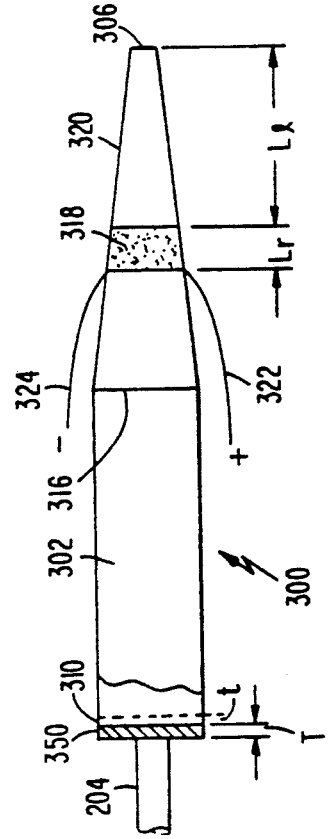

LASER DEVICE WITH INTERMEDIATE REFRACTION INDEX LAYER FOR REDUCED FRESNEL LOSSES

FIELD OF THE INVENTION

This invention relates generally to a laser device utilizing laser light energy conveyed along an optic fiber to a tip element for emission therefrom, and more particularly to a surgical laser device in which laser light is transmitted from the fiber into a treated laser light-receiving surface of the tip element with significantly lowered Fresnel losses at an interface therebetween.

BACKGROUND OF THE PRIOR ART

Known contact surgical devices which utilize laser light as energy for ablation or vaporization of tissue can generally be divided into two categories: devices which have a tip formed of a ceramic material such as YAG, sapphire or silica, different from the material of an optic fiber carrying laser light to the tip, and devices in which an end of the optic fiber itself is tapered or otherwise sculpted to a shape useful for surgical applications. Devices of both types offer unique advantages, but also pose certain problems in their manufacture and subsequent use.

The tip element can be manufactured in a wide range of shapes and sizes, but experience shows that for substantial rates of transfer of laser energy from the optic fiber to the tip, heating of the fiber/tip interface due to Fresnel losses requires cooling. Such cooling can be provided by a fluid flow to transfer heat from the interface. However, such devices tend to be cumbersome, restrict the surgeon's freedom of operation, and can increase the risk to the patient.

The tapered fiber end devices require no cooling because there is no abrupt change of refractive index at an interface where energy losses and localized heating can occur but, for practical reasons, there are limitations on the size and shape to which the fiber end can be formed. For surgically useful sizes, such tips can only be formed at the light delivery ends of relatively large fibers which tend to be inflexible.

Known devices in which laser light is conveyed through an optic fiber to a tip made of a material having a significantly different refractive index include Daikuzono U.S. Pat. No. 4,736,743, in which laser energy delivered from a conically tapered probe is used to vaporize tissue in local contact therewith. Another such surgical laser probe is taught in also Daikuzono U.S. Pat. No. 4,693,244.

There exists a need for a surgical device in which laser light is delivered from a laser energy source through an optic fiber to a tip element without the need for cooling an interface between the delivery end of the optic fiber and the laser light receiving end of the tip element.

SUMMARY OF THE DISCLOSURE

A principal object of the present invention is to provide a laser device in which laser light energy passes from a delivery end of an optic fiber into a treated light-receiving end surface of a tip element with very low Fresnel losses at the fiber/tip interface.

Another related object of this invention is to provide an efficient surgical device for directed emission of laser light from a light-delivering end of a tip element thereof.

It is a further object of this invention to provide a treatment for a laser light delivering tip element so as to reduce Fresnel losses between a laser light delivering optic fiber end and a laser light receiving surface of the tip element.

It is an even further related object of this invention to provide a method for reducing Fresnel losses at an interface between a laser light transmitting end of an optic fiber and a laser light transmitting element.

These and other objects of the present invention are realized by providing an improved laser device, in which laser light energy is conveyed from a laser energy source through an optic fiber formed of a first material which has a first refractive index into a laser light receiving tip element formed of a second material which has a second refractive index, wherein the improvement includes the provision of a layer formed at the laser light receiving end of the tip element, the layer comprising a third material which has a non-abruptly varying refractive index which is graded between the magnitudes of the first and second refractive indices.

In another aspect of this invention, there is provided an improved method for reducing Fresnel losses where laser light energy is transmitted from one end of an optic fiber having a first refractive index into a laser light receiving tip element formed of a second material having a second and relatively higher refractive index, the improvement comprising the provision of a layer formed at a laser light receiving end of the tip element, the layer comprising a third material having a non-abruptly varying refractive index which is graded between the magnitudes of the first and second refractive indices.

BRIEF DESCRIPTION OF THE DRAWINGS

FIGS 6A and 6B, respectively, are a partially sectioned side view and an end view (in the direction of arrow F) of a third embodiment of the present invention.

FIG. 7 is a partially sectioned side view of a laser light emitting tip element, generally similar in shape to the embodiment illustrated in FIGS. 5A and 5B, also including an ohmic heating layer provided for controlled ohmic heating at a selected portion of the laser light delivering tip element.

FIG. 8 is a partially sectioned side view of a laser light emitting tip element generally similar in shape to the embodiment illustrated in FIGS. 5A and 5B, provided with a laser light absorbing material on a portion of the tip element.

DESCRIPTION OF THE PREFERRED EMBODIMENTS

Figure 1:
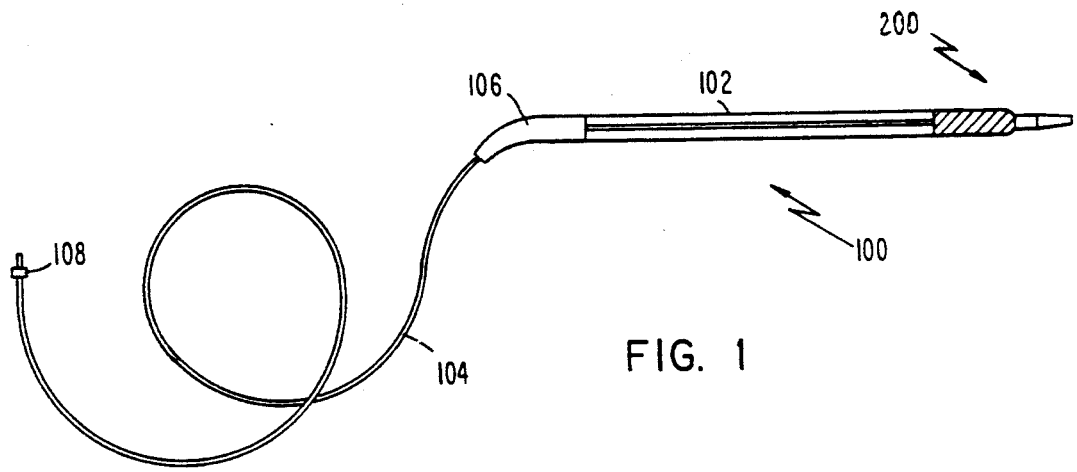
FIG. 1 schematically illustrates elements of an exemplary apparatus by which laser light energy received from a laser energy source is conveyed to a laser light wetting tip for surgical procedures.

A surgeon employing laser energy for surgical purposes typically holds in his hand a lightweight handpiece (not shown) into which fits an elongate assembly having a tip element emitting laser light energy for cutting, cauterizing and/or coagulating tissue on which he is operating. As best understood with reference to FIG. 1, such a hand-held assembly 100 has a slim, elongate body 102 connected to a flexible element 104 at a junction 106. The flexible element 104 comprises an outer tubular sheath protectively containing a suitable length of an optic fiber connected by a junction 108 at one end to a source of laser energy (not shown). Laser light energy of a suitable wavelength is received at junction 108 from a laser source located at a distance from the patient and is conveyed by internal reflection within the optic fiber to be delivered through a delivery end 200 of hand-held element 100.

Figure 2:
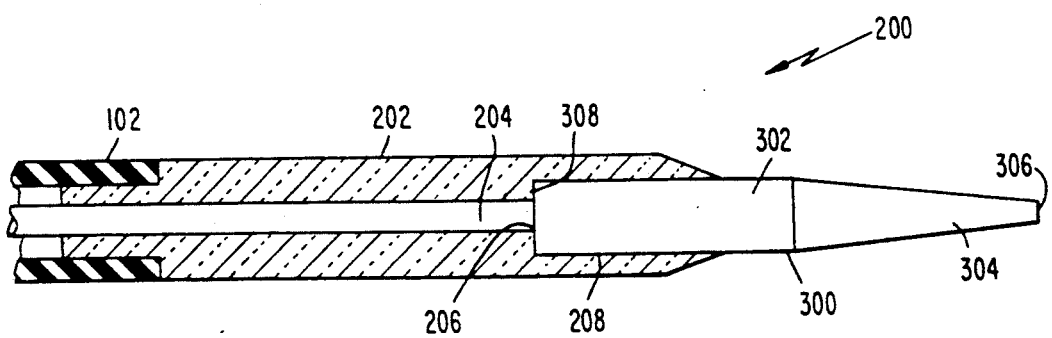
FIG. 2 is a partially-sectioned enlarged view illustrating details at the tip end of the apparatus of FIG. 1.

As illustrated in FIG. 2, delivery end 200 of the device at a forward end of elongate element 102 is connected in known fashion to a fiber/tip connector 202 which is preferably made of stainless steel or other readily sterilizable material. An optic fiber 204 is passed into fiber/tip connector 202 so that laser light energy conveyed by internal reflection through optic fiber 204 is deliverable through an end face 206. The fiber/tip connector 202 is formed with a cylindrical recess 208 at its forward end. Received therein is one end of a tip element 300, to receive laser light energy from optic cable 204.

Figure 3A:
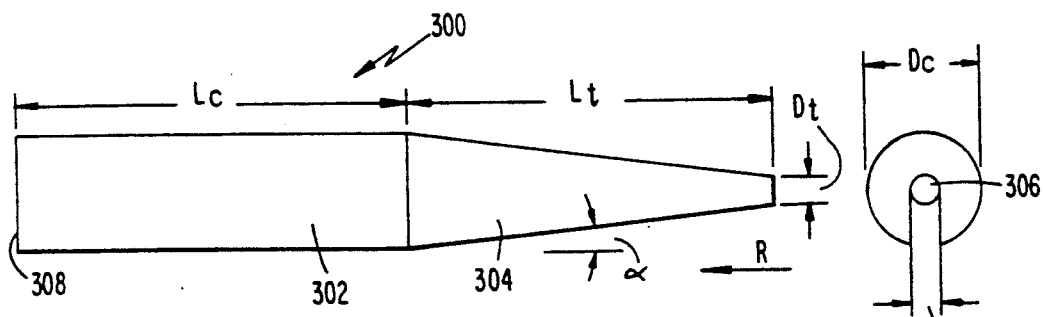
FIGS. 3A and 3B are, respectively, a side view and an end view (in the direction of arrow R) of a conveniently shaped laser light emitting tip element.
Figure 3B:
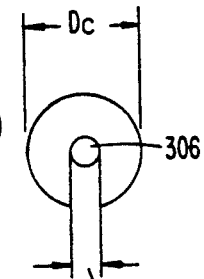

Referring now to FIGS. 3A and 3B, tip element 300, according to a preferred embodiment of the present invention, has a cylindrical portion 302 of length "$L_c$" and a coaxially tapered portion 304 of length "$L_t$" which ends at its smallest cross-section portion at a laser light delivery end surface 306. At the other end of tip element 300 is a laser light receiving surface 308 which is typically epoxied directly to the laser light delivery end surface 206 of optic fiber 204 with a clear epoxy glue, e.g., EPO-TEK 301-2.

As illustrated in FIG. 3B, the maximum diameter of tip element 300 is "$D_c$" and the minimum diameter, at the laser light delivery end surface 306 is "$D_t$". The external surface of tapered portion 304 is conical in shape and is inclined at an angle "$\alpha$" with respect to the cylindrical surface of portion 302. "$\alpha$" preferably is between 6° and 15°.

Other shapes, e.g., a right cylinder of circular or other cross-section, or a combination of a cylinder and an end portion with a rounded end, etc., may be employed to suit specific needs as broadly disclosed herein. The detailed discussions of beneficial surface treatments provided at the light receiving and energy delivery end of the tip element therefore have broad applicability, by logical extension of the same inventive principle, regardless of the shape of the tip element body through which laser light energy is transmitted thereafter.

Tip element 300 is preferably made of a clear crystalline material, e.g., a ceramic material such as YAG, sapphire or silica. Any known techniques may be used to form the selected material into the final shape of tip element 300. It is important, however, that end surfaces 206 and 308 be made smooth and clear to transmit laser light therethrough, i.e., from optic fiber 204 into tip element 300. Also, side surfaces 304 and 306 of tip element 300 are smooth to facilitate internal reflection as well as ion beam mixing or ion beam enhanced deposition of a selected material for laser light absorption thereat according to certain embodiments. The precise lengths and diameters of various portions of tip element 300 may be selected by persons of ordinary skill in the art to suit the specific operational needs to be served by the device, e.g., as a scalpel or a cauterizer.

Relevant properties of the materials of interest are tabulated in Table 1 below.

TABLE 1

| | Melting Point (°C.) | Thermal Conductivity (W/m·°C.) | Refractive Index at 1.06 μm Wavelength |
|---|---|---|---|
| Sapphire ($Al_2O_3$) | 2300 | 35 | 1.75 |
| Silica ($SiO_2$) | 1740 | 7 | 1.54 |
| YAG ($Y_3Al_5O_{12}$) | 2220 | 13 | 1.82 |

Regardless of the shape and size of tip element 300, the safety of the patient and the convenience of the surgeon both require minimization of energy losses within the device. To avoid the need to cool the interface between optic fiber 204 and cylindrical portion 302 of tip element 300, structure must be provided there to reduce so-called "Fresnel losses". Such losses can, in principle, be reduced by providing a conventional antireflection coating, but this has been found to be inadequate in terms of both reliability and durability.

Note that optic fiber 204 is bonded at its outside surface to the inside surface of the hole in fiber/tip connector element 202. The refractive index of the epoxy material used for such purposes is equal to or greater than that of silica, but is less than that of the material of which the tip element is made. The epoxy must also be transparent to the wavelength(s) of the laser light used. The glass transition temperature of the epoxy preferably should be approximately 200° C. to assure a strong bond even if the connector should become hot during, for example, prolonged use. It is also possible to bond the fiber/tip connector 202 to the tip element 300 with an epoxy material which is not transparent, but is stronger and has a higher glass transition temperature. Suitable epoxy materials are commercially available.

The length of the epoxy bond between the laser light delivery end of the optic fiber 204 and the fiber/tip connector 202 should be made such that they bond strongly and the fiber will not disconnect even if subjected to quite severe lengthwise forces during use or handling of the device. Persons skilled in the mechanical arts should be able to determine such parameters in light of the epoxy material, operational temperatures desired and the like, hence more precise details are not specified here.

Although the term "optic fiber" is utilized in this discussion, there is no reason why, at least in principle, one cannot utilize a multi-strand optic fiber in place of a monofilament optic fiber 204 as illustrated. Similarly, materials other than ceramic materials such as YAG, sapphire or silica may be used to form tip element 300 and its shape may be formed by turning and polishing an element of the selected material. Depending on its size and other specific needs, the body of tip element 300 may be molded or grown as a shaped crystal. In any case, the cylindrical, tapered and end surfaces of tip element 300 should be made smooth to facilitate internal reflection and to minimize heating due to laser light absorption thereat except where such absorption is desired and is intentionally provided as described hereinafter.

Material used to form optic fiber 204, e.g., silica, typically has a refractive index in the range 1.4 to 1.55, and materials suitable for forming tip element 300, e.g., ceramic materials such as silica, YAG and sapphire, typically have refractive indices within the range 1.4 to 1.85. It is thus readily seen that laser light which travels by internal reflection along optic fiber 204 moves from a region of relatively low refractive index and into a region of relatively higher refractive index upon entry into tip element 300. It is believed that it is this sudden change in refractive indices, going from a relatively low refractive index (optic fiber), to a relatively high refractive index material in the tip element (e.g., sapphire), which causes significant local losses (generally referred to as "Fresnel losses") at the fiber/tip interface with undesirable heating thereat.

In a preferred embodiment of the present invention, a thin region 310 having a graded refractive index and comprising a varying concentration of suitable material, e.g., silica, of a thickness "t", is provided at the laser light receiving end surface 308 of tip element 300. See FIGS. 4B and 4D. It is important that the material constituting region 310 have a refractive index varying between the respective refractive indices of optic fiber 204 and tip element 300. Ideally, such a region should have a refractive index at its outermost surface 308 equal in magnitude to that of the optic fiber 204 and changing non-abruptly over the thickness "t" to a magnitude equal to that of the material of which the bulk of tip element 300 is formed, e.g., ceramic materials such as YAG or sapphire.

Figure 4A:
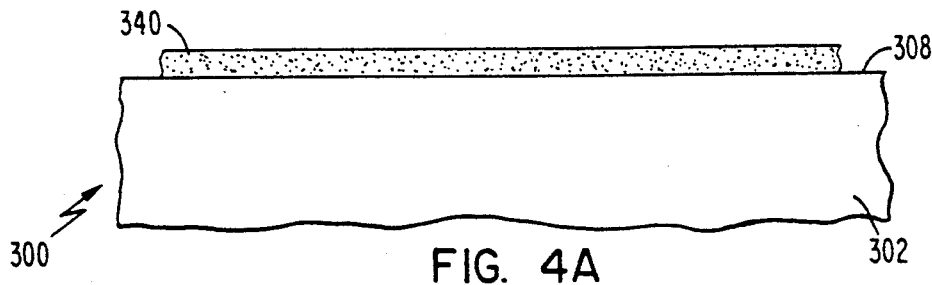
FIGS. 4A and 4B are schematic illustrations depicting stages in the treatment applied at the laser light-receiving end surface of the tip element by an ion beam mixing process and FIGS. 4C and 4D for an ion beam enhanced deposition process, respectively, to generate a region in which a refractive index is graded between the magnitudes of the refractive indices of the materials of an optic fiber and a tip element.
Figure 4B:
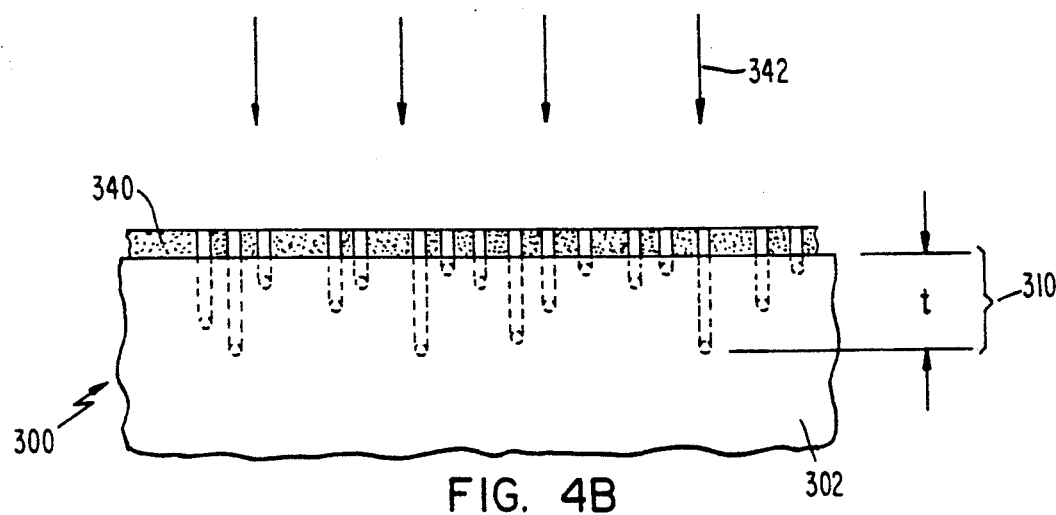
Figure 4C:
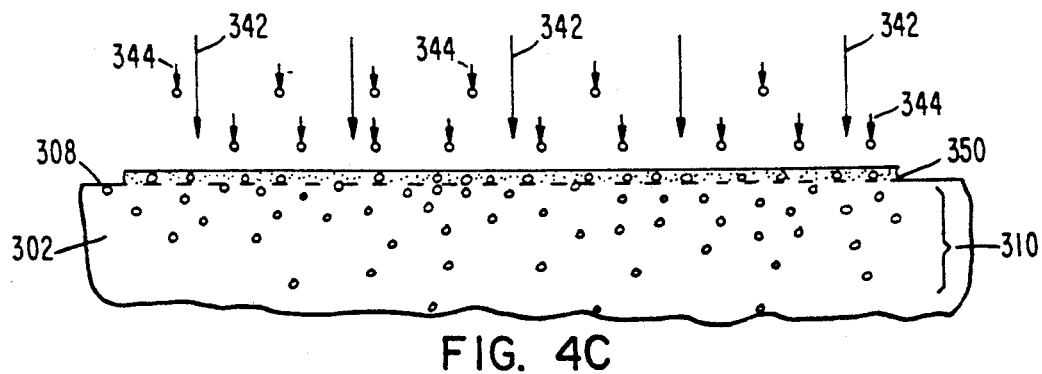
Figure 4D:
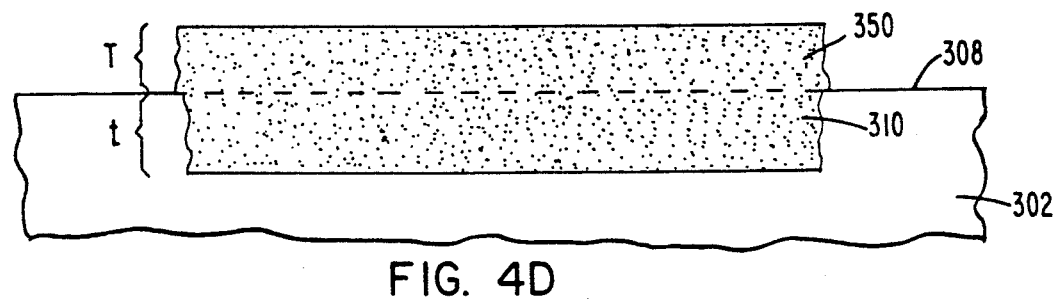
Figure 5B:
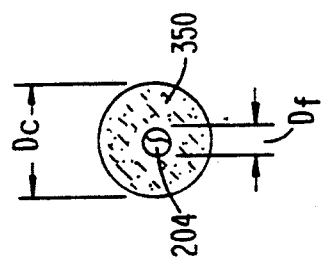
FIGS. 5A and 5B, respectively, are a side view and an end view (in the direction of arrow F) of a laser light delivering end tip element provided with an intermediate graded refraction index layer and an added layer of silica at a light receiving end according to a preferred embodiment of this invention.
Figure 5A:
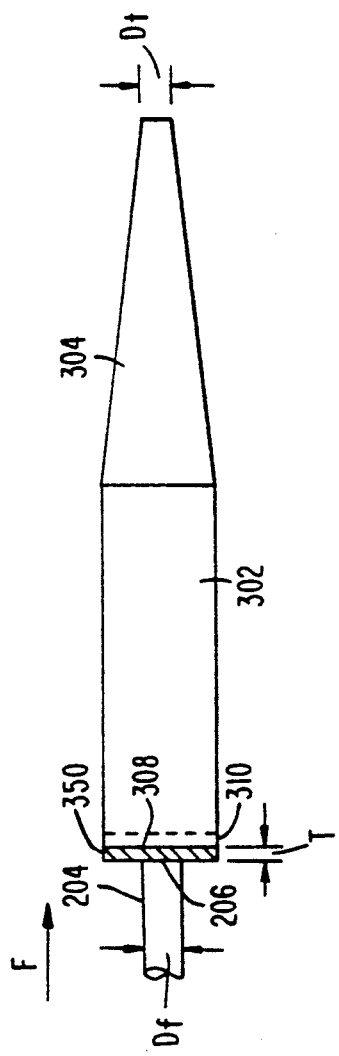

It is found that the incorporation of small amounts of a selected ceramic-type material, such as $SiO_2$ within the material of tip element 300, e.g., ceramic materials such as YAG or sapphire, in the region immediately adjacent the physical end surface 308, creates such a region, illustrated in FIGS. 4B and 4D as a layer 310, of the desired non-abruptly varying refractive index and thickness. This is most conveniently accomplished by either of two processes commercially developed by Beamalloy Corporation, of Dublin, Ohio, and hitherto employed for other advantageous results, e.g., to create a hard surface region. These processes are known in the art as the "ion beam mixing process" and the "ion beam enhanced deposition process", respectively. A suitable thickness for such an intermediate graded refractive index layer 310 is in the range 50Å to 10,000Å..

In the "ion beam mixing process" a thin film 340, 1000Å or less in thickness, of a selected material, e.g. silica, is deposited on the light-receiving surface 308 of tip element 300 by any known technique such as sputtering or the like. See FIG. 4A. This film 340 is then subjected to illumination by an ion beam 342 comprising ions of an inert gas such as argon, xenon or krypton, or neon. The energetic impacts of such ions drives the silica from film 340 into the YAG or sapphire material of tip element 300. See FIG. 4B. With the proper choice of implant parameters, e.g., the film material, its thickness, the ion species and energies (in KeV), and the time for which the ion beam is applied, the entire deposited film can be implanted/mixed into, i.e., "alloyed" with, the substrate or target material.

Naturally, the concentration of the "implanted" or "mixed-in" material diminishes within layer or region 310 from the outside surface 308 into the tip element material in a non-abrupt manner. Consequently, the refractive index across the thickness "t" thereof also varies in a non-abrupt manner, changing from that of the film material to that of the tip element material. Thus, if silica is the chosen film material, laser light from a silica optic fiber 204 will not encounter an abrupt change in refractive index and no Fresnel losses will occur as the laser light passed through the varying refractive index layer 310 into the body of tip element 300.

Another very significant advantage is that the layer 310 provided in this manner is alloyed with and remains very much a part of the tip element and will not delaminate or peel away therefrom during subsequent thermal cycling of the tip element in use.

In the "ion beam enhanced deposition process" the provision of selected material, e.g., silica 344, and the ion beam bombardment thereof, both occur simultaneously. This results in a silica layer 350 that is grown on the surface and is continuously and simultaneously modified by the ions energetically driving the silica across the surface 308 into the material of tip element 300 to form a layer 310 having the desired properties, i.e., varying and graded refractive index and no likelihood of delamination. For simplicity and convenience this is schematically illustrated in FIG. 4D, for both the "ion beam mixing process" and the "ion beam enhanced deposition process". Deutchman et al. U.S. Pat. No. 4,992,298, titled "Dual Ion Beam Alloying Process", describes apparatus and a method for one form of the "ion beam enhanced deposition process" as described herein and is incorporated herein by reference for additional related details disclosed therein.

It may be even more advantageous to apply an additional thin film 350 of silica of thickness "T" to layer 310 to be contiguous therewith, as illustrated schematically in FIG. 4D. Such an added silica layer 350 will be very securely bonded to the silica-rich surface 308 into which silica has previously been implanted to form the graded refractive index layer 310 of thickness "t".

Silica layer 350 can, in practice, be added after the "ion beam mixing process" is completed. However, as a matter of production efficiency, this is best accomplished by the "ion beam enhanced deposition process" by simply continuing to deposit silica after reducing the energy level in the ion beam until the desired final thickness of silica layer 350 is obtained. When this is done, the result is a strong secure bond between layer 350 of silica to the varying refractive index layer 310 forming the light-receiving end of tip element 300. See FIG. 4D.

FIGS. 6A and 6B depict yet another embodiment of the present invention. In this variation, the laser light energy delivering end of optic fiber 204 is enlarged, e.g., by localized heating and deformation, so that it has an enlarged diameter end portion 212 which contacts intermediate refractive index layer 310 over a correspondingly larger area. It will be readily seen from FIG. 6B that "$D_e$", the diameter of the enlarged end of optic fiber 204, is larger than the diameter "$D_f$" of the rest of the optic fiber.

In all of the embodiments described hitherto, a controlled flow of laser light is emitted from surface 306 at the forwardmost point of laser tip 300. Typically, such laser light emissions may be utilized to ablate or vaporize material, e.g., body tissues of a patient, immediately in front of surface 306. The rate at which this can be accomplished is determined by the rate at which the energy is provided to the tissue and by whether or not the tissue in question is in direct contact with the surface through which the energy is transmitted into the tissue. For certain applications, e.g., the ablation of diseased dental material of a tooth, actual contact between an energy emitting surface and the tissue to be ablated may not be required or advisable. However, physical contact between an energy providing surface and soft body tissue may be desirable in other applications, e.g., for cauterization. Relatively low laser energy transfers may also be required to cause local heating and coagulation of blood at and around surgical sites.

For certain applications, it may be desirable to have a portion of the tip element delivering emitted laser light received therein to perform ablation/vaporization of tissue while, at the same time, providing controlled ancillary local heating at a portion of the tapered surface of the tip element. FIG. 8 depicts a structure of an embodiment suitable for this purpose. In this embodiment, between end face 306 and the peripheral line 316 at which cylindrical portion 302 joins tapered portion 304 there is provided a surface layer 318 of an electrically resistive material deposited in any known manner. For purposes of illustration, the electrically resistive layer 318 is shown in FIG. 7 as having an axial length "$L_r$" with a length "$L_f$" left as an unlayered portion 320 of the tip element 300 extending to the laser light emitting surface 306. Electrical leads 322 and 324 are illustrated only schematically in FIG. 8 and may be formed and disposed in any known manner, with suitable insulation, e.g., a silica layer, provided thereover to avoid generating electrical currents between them through surrounding tissue.

During operation of such a device, the surgeon can selectively provide ablative/evaporative energy flows by emission of laser light energy from surface 306 forwardly of tip element 300. Also, as and when appropriate, by forcible sideways contact between the electrically heated resistive surface 318 and body tissues, he or she can be cauterizing or coagulating tissue at the tapered side of tip element 300. The amount of "ohmic heating" generated in electrical resistive layer 318 is determined by its electrical resistance and by the electrical current passed therethrough under the surgeon's control. Such parameters may be selected to be commensurate with the surgeon's needs.

Finally, FIG. 8 depicts yet another embodiment of this invention in which, as in all the other embodiments described above, the provision of an intermediate refractive index layer 310 reduces Fresnel losses and efficiently delivers laser light energy to the tapered front end 304 of tip element 300. In this embodiment, an entire end portion of tapered portion 304, including front end surface 306, is provided a coating of a high temperature melting point material such as titanium, chromium, nickel, zirconium, molybdenum, tantalum, tungsten, yttria, zirconia or alumina.

This constituent is preferably provided by either one of the ion beam mixing and the ion beam enhanced deposition processes, as previously described, except for the obvious differences in implanted material and related physical parameters, to form a strong metallic/ceramic bonded layer which does not readily detach from the parent material of tip element 300 during prolonged use. With such a structure, laser light energy is emitted from optic fiber 204, passes with minimal Fresnel losses through intermediate refractive index layer 310 into cylindrical portion 302 and then into tapered portion 304. There is, inevitably, some spreading of the beam of laser light in its transmission through cylindrical portion 302 and an adjacent first part of tapered portion 304, as indicated in FIG. 8 by the arrowed broken lines. With knowledge of the various geometric dimensions of tip element 300 and the refractive index of the material forming the same, it should be easy for a person of ordinary skill in the art to compute where the beam of diverging laser light within tip element 300 will be incident at the tapered surface of portion 304. The layer 326 can then be formed to cover at least that portion of the tapered surface which will receive this somewhat diverging laser light beam. Details of such a structure are provided in our contemporaneously filed co-pending application U.S. Ser. No. 07/72,3987, which is incorporated herein by reference for relevant disclosure therein.

Any wavelength of laser light can be utilized in the device by selecting an appropriate high temperature melting point material to be deposited into and/or over the material of tip element 300 to form the laser light energy absorbing layer 326. For example, tungsten absorbs not only the visible portion of the electromagnetic spectrum but also the infra-red. Hence with tungsten as the chosen high temperature melting point material for layer 326 the disclosed device can be readily used with both visible and infra-red type laser sources, with commensurate choice of output, performance and utility. The key to success here is that all of the laser light energy conveyed via the body of tip element 300 to layer 326 is absorbed and converted to heat thereat.

In the absence of layer 326, the laser light beam internally incident on the smooth tapered surface of portion 304 will simply internally reflect and continue forward toward end surface 306. Layer 326 containing a high temperature melting point constituent, however, readily absorbs the incident laser light and converts its energy into heat. Consequently, the entire surface of tapered portion 304 which is covered by layer 326 (including end face 306), becomes heated solely by absorbing laser light energy received from optic cable 204. This heated surface 326 can be used by the surgeon to locally apply heat to body tissues for vaporization, cauterization or coagulation as desired. Because the laser light in this embodiment is not directly emitted onto body tissue to be absorbed thereby, this embodiment does not raise local tissue temperatures to the point at which the tissue material vaporizes very rapidly. For certain applications, this is highly desirable. Note that this embodiment allows a surgeon to utilize an existing laser energy source, to efficiently apply the energy provided thereby without any laser light emission, in a different manner to obtain commensurately different operational results.

In summary, there are disclosed in this application various embodiments of the structure of a laser device tip element whereby energy from a laser energy source may be delivered precisely at selected locations at controlled rates. The described structure of each of these embodiments ensures significant reduction of Fresnel losses where the optic fiber meets the tip element, without the need for cumbersome and complicated cooling means. This facilitates the user's handling of the hand-held energy-delivering element. The different embodiments disclosed herein further provide a wide array of useful applications of a common basic geometry. Consequently, once surgeons become familiar with handling of the tapered tip element, they may, without serious modification of their operating techniques, obtain a variety of desired results by appropriate selection of one or more of the disclosed embodiments.

In this disclosure, there are shown and described only the preferred embodiments of the invention, but, as aforementioned, it is to be understood that the invention is capable of use in various other combinations and environments and is capable of changes or modifications within the scope of the inventive concept as expressed herein.

What is claimed is:

1. An improved laser device, in which laser light energy is conveyed from a laser energy source through an optic fiber formed of a first material having a first refractive index into a laser light receiving tip element formed of a second material having a second refractive index, the improvement comprising:
   a first layer formed at a laser light receiving end of the tip element, the first layer comprising a third material having a non-abruptly varying refractive index intermediate the magnitudes of the first and second refractive indices.

2. The laser device according to claim 1, wherein:
   the third material comprises a selected constituent incorporated into the second material at the laser light receiving end of the tip element to a predetermined depth in a non-abruptly varying concentration, to thereby form a region of non-abruptly varying refractive index of a corresponding predetermined thickness thereat.

3. The laser device according to claim 2, wherein:
   said constituent is applied by an ion beam mixing process for said incorporation thereof into the second material at the laser light receiving end of the tip element.

4. The laser device according to claim 2, wherein:
   said constituent is applied by an ion beam enhanced deposition process for said incorporation thereof into the second material at the laser light receiving end of the tip element.

5. The laser device according to claim 3, wherein:
   said constituent comprises a ceramic material.

6. The laser device according to claim 4, wherein:
   said constituent comprises a ceramic material.

7. The laser device according to claim 2, wherein:
   said constituent is the same as said first material.

8. The laser device according to claim 7, wherein:
   said first material is silica and said second material comprises one of YAG or sapphire.

9. The laser device according to claim 2, wherein:
   the predetermined thickness of the first layer is in the range 50Å to 10,000Å.

10. A laser device for conveying laser light energy from a laser energy source, comprising:
    a length of optic fiber formed of a material having a first refractive index, having a laser light receiving end for receiving laser light energy from the energy source and a laser light delivery end for delivering laser light energy therefrom;
    a tip element formed of a material having a second refractive index, having a first end positioned for receiving laser light energy from the laser light delivery end of the optic fiber and a second end from which laser light energy is emitted during use of the device; and
    a layer formed at the first end of the tip element, the layer having a non-abruptly varying refractive index intermediate the magnitudes of the first and second refractive indices.

11. The laser device according to claim 10, wherein:
    the layer comprises a constituent incorporated into the material of the first end of the tip element to a predetermined depth to thereby form a non-abruptly changing refractive index region of a corresponding predetermined thickness thereat.

12. The laser device according to claim 11, wherein:
    the constituent is applied by an ion beam mixing process.

13. The laser device according to claim 11, wherein:
    the constituent is applied by an ion beam enhanced deposition process.

14. The laser device according to claim 12, wherein:
    the constituent comprises a ceramic material.

15. The laser device according to claim 13, wherein:
    the constituent comprises a ceramic material.

16. The laser device according to claim 11, wherein:
    the predetermined thickness of the layer is in the range 50Å to 10,000Å.

17. The laser device according to claim 10, further comprising:
    a cylindrical sleeve connected to the first end of the tip element, comprising a fourth material and having an inside diameter sized to closely receive therein the laser light energy delivery end of the optic fiber.

18. The laser device according to claim 10, wherein:
    the laser light energy delivery end of the optic fiber is locally enlarged to have an end face of a diameter larger than a diameter of the optic fiber substantially along its length.

19. The laser device according to claim 10, wherein:
    the tip element has a cylindrical portion of a predetermined length $L_c$ extending in a forward direction from the layer and a coaxial tapered portion of a predetermined length $L_t$ extending forwardly of the cylindrical portion to a forward end surface, the tapered portion having an external surface inclined at a predetermined angle with respect to an axis of the tip element.

20. The laser device according to claim 19, wherein:
    said angle is in the range 6° – 15°.

21. The laser device according to claim 19, further comprising:
    an ohmic heating layer of an electrically resistive material on a portion of the inclined surface of the tapered portion of the tip end; and
    means for providing an electrical current to the ohmic heating layer.

22. The laser device according to claim 21, wherein:
    the ohmic heating layer has an axial length $L_r$, which is less than the length $L_t$ of the tapered portion and covers only an intermediate portion of the tapered portion of the tip end.

23. The laser device according to claim 19, further comprising:
    a laser light absorbing layer provided on the inclined surface and the forward end surface of the tip element, whereby all laser light energy reaching the laser light absorbing layer through the material of the tip element is absorbed therein and is converted locally into heat.

24. The laser device according to claim 23, wherein:
the laser light absorbing layer comprises a constituent selected from the group of high temperature melting point materials consisting of titanium, chromium, nickel, zirconium, molybdenum, tantalum, tungsten, yttria, zirconia and alumina.

25. The laser device according to claim 24, wherein:
said constituent is applied by an ion beam mixing process to become incorporated into the material of the tip element.

26. The laser device according to claim 24, wherein:
said constituent is applied by an ion beam enhanced deposition process to become incorporated into the material of the tip element and to form an additional layer of the constituent which is securely bonded with the tip element.

27. The laser device according to claim 16, wherein:
the tip element comprises a material selected from the group of ceramic materials such as YAG, silica and sapphire; and
the laser light absorbing layer forms a ceramic-metal alloy with the material of the tip element.

28. A method for reducing Fresnel losses in a laser device in which laser light energy is provided from one end of an optic fiber formed of a first material having a first refractive index into a laser light receiving tip element formed of a second material having a second and relatively higher refractive index, wherein the improvement comprises the step of:
providing a layer at a laser light receiving end surface of the tip element, the layer comprising a third material having a non-abruptly varying refractive index of a magnitude intermediate the magnitudes of the first and second refractive indices.

29. The method according to claim 28, wherein:
the step of providing the layer comprises the step of applying a selected constituent by ion beam mixing at the laser light receiving end surface of the tip element, to incorporate the constituent into the tip element to a predetermined depth in a non-abruptly varying concentration and to form a layer contiguous therewith of the constituent material to a corresponding predetermined thickness and bonded securely to the tip element thereat.

30. The method according to claim 28, wherein:
the step of providing the layer comprises the step of applying a selected constituent by ion beam enhanced deposition at the laser light receiving end surface of the tip element, to incorporate the constituent into the tip element to a predetermined depth in a non-abruptly varying concentration and to form a layer contiguous therewith of the constituent material to a corresponding predetermined thickness and bonded securely to the tip element thereat.

31. The method according to claim 29, wherein:
said constituent is a ceramic material.

32. The method according to claim 30, wherein:
said constituent is a ceramic material.

33. A method for reducing Fresnel losses in a laser device in which laser light energy is provided from one end of an optic fiber formed of a first material having a first refractive index into a laser light receiving surface of a tip element formed of a second material having a second and relatively higher refractive index, wherein the improvement comprises the step of:
passing the laser light through a third material having a non-abruptly varying refractive index of a magnitude intermediate the magnitudes of the first and second refractive indices, wherein said third refractive index varies from a value corresponding to that of the refractive index of the first material to a value corresponding to that of the refractive index of the second material in a direction directed into the tip element from the light receiving surface of the tip element.

34. An improved laser device, in which laser light energy is conveyed from a laser energy source through a first element formed of a first material having a first refractive index into a laser light receiving second element formed of a second material having a second refractive index, the improvement comprising:
a layer formed at a laser light receiving end of the second element, the layer comprising a third material having a non-abruptly varying refractive index intermediate the magnitudes of the first and second refractive indices.

35. A laser device for conveying laser light energy from a laser energy source, comprising:
a first element formed of a material having a first refractive index, having a laser light receiving end for receiving laser light energy from the energy source and a laser light delivery end for delivering laser light energy therefrom;
a second element formed of a material having a second refractive index, having a first end positioned for receiving laser light energy from the laser light delivery end of the first element and a second end from which laser light energy is emitted during use of the device; and
a layer formed at the first end of the second element, the layer having a non-abruptly varying refractive index intermediate the magnitudes of the first and second refractive indices.

36. A method for reducing Fresnel losses in a laser device in which laser light energy is provided from one end of a first element formed of a first material having a first refractive index into a laser light receiving second element formed of a second material having a second refractive index, wherein the improvement comprises the step of:
providing a layer at a laser light receiving end surface of the second element, the layer comprising a third material having a non-abruptly varying refractive index of a magnitude intermediate the magnitudes of the first and second refractive indices.

* * * * *